(12) United States Patent
Guerrera et al.

(10) Patent No.: US 11,497,501 B2
(45) Date of Patent: Nov. 15, 2022

(54) CIRCULAR STAPLING DEVICE WITH A-FRAME SPLINES

(71) Applicant: Covidien LP, Mansfield, MA (US)

(72) Inventors: Joseph Guerrera, Watertown, CT (US); Charlie Kollar, West Hartford, CT (US); Patrick Mozdzierz, Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 953 days.

(21) Appl. No.: 15/935,260

(22) Filed: Mar. 26, 2018

(65) Prior Publication Data

US 2019/0290284 A1 Sep. 26, 2019

(51) Int. Cl.
*A61B 17/115* (2006.01)
*A61B 17/00* (2006.01)

(52) U.S. Cl.
CPC . *A61B 17/1155* (2013.01); *A61B 2017/00389* (2013.01); *A61B 2017/00477* (2013.01)

(58) Field of Classification Search
CPC ...... A61B 17/1155; A61B 2017/00389; A61B 2017/00477
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated Jul. 31, 2019, issued in EP Appln. No. 19164825.

*Primary Examiner* — Anna K Kinsaul
*Assistant Examiner* — Daniel Jeremy Leeds

(57) ABSTRACT

A surgical stapling device includes an anvil assembly and a shell assembly having a shell housing including a plurality of shell splines having an A-frame configuration. The shell splines include a triangular tip that defines an apex and is positioned to engage splines on an anvil shaft of the anvil assembly to properly align the anvil assembly with the shell assembly. The A-frame splines are spaced from each other to define primary channels that are dimensioned to receive the splines of the anvil assembly to properly align the anvil assembly with the shell assembly. The A-frame splines also define secondary channels that are positioned proximally of and in axial alignment with the apex of the A-frame splines. In situations in which an apex of the splines on the anvil assembly "crash" into the apex of the A-frame splines of the shell assembly, i.e., the apexes of the splines meet head on, the A-frame splines of the shell assembly are constructed to fracture to allow the splines of the anvil assembly to penetrate into the A-frame splines and pass into the secondary channels of the A-frame splines to properly align the anvil assembly with the shell assembly of the stapling device.

20 Claims, 11 Drawing Sheets

(56) References Cited

U.S. PATENT DOCUMENTS

| | | | |
|---|---|---|---|
| 4,198,982 A | 4/1980 | Fortner et al. | |
| 4,207,898 A | 6/1980 | Becht | |
| 4,289,133 A | 9/1981 | Rothfuss | |
| 4,304,236 A | 12/1981 | Conta et al. | |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A | 10/1984 | Kanshin et al. | |
| 4,485,817 A | 12/1984 | Swiggett | |
| 4,488,523 A | 12/1984 | Shichman | |
| 4,505,272 A | 3/1985 | Utyamyshev et al. | |
| 4,505,414 A | 3/1985 | Filipi | |
| 4,520,817 A | 6/1985 | Green | |
| 4,550,870 A | 11/1985 | Krumme et al. | |
| 4,573,468 A | 3/1986 | Conta et al. | |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,632,290 A | 12/1986 | Green et al. | |
| 4,646,745 A | 3/1987 | Noiles | |
| 4,665,917 A | 5/1987 | Clanton et al. | |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,717,063 A | 1/1988 | Ebihara | |
| 4,752,024 A | 6/1988 | Green et al. | |
| 4,754,909 A | 7/1988 | Barker et al. | |
| 4,776,506 A | 10/1988 | Green | |
| 4,817,847 A | 4/1989 | Redtenbacher et al. | |
| 4,873,977 A | 10/1989 | Avant et al. | |
| 4,893,662 A | 1/1990 | Gervasi | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,271,543 A * | 12/1993 | Grant | A61B 17/115 227/179.1 |
| 5,271,544 A | 12/1993 | Fox et al. | |
| 5,275,322 A | 1/1994 | Brinkerhoff et al. | |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A * | 9/1994 | Blanco | A61B 17/115 227/19 |
| 5,350,104 A * | 9/1994 | Main | A61B 17/115 227/179.1 |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,464,415 A | 11/1995 | Chen | |
| 5,470,006 A | 11/1995 | Rodak | |
| 5,474,223 A | 12/1995 | Viola et al. | |
| 5,497,934 A | 3/1996 | Brady et al. | |
| 5,503,635 A | 4/1996 | Sauer et al. | |
| 5,522,534 A | 6/1996 | Viola et al. | |
| 5,533,661 A | 7/1996 | Main et al. | |
| 5,588,579 A | 12/1996 | Schnut et al. | |
| 5,609,285 A | 3/1997 | Grant et al. | |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,749,896 A | 5/1998 | Cook | |
| 5,758,814 A | 6/1998 | Gallagher et al. | |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,024,748 A | 2/2000 | Manzo et al. | |
| 6,050,472 A | 4/2000 | Shibata | |
| 6,053,390 A | 4/2000 | Green et al. | |
| 6,068,636 A | 5/2000 | Chen | |
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,142,933 A | 11/2000 | Longo et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 | 2/2001 | Billner et al. | |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,258,107 B1 * | 7/2001 | Balazs | A61B 17/115 227/175.1 |
| 6,264,086 B1 | 7/2001 | McGuckin, Jr. | |
| 6,269,997 B1 | 8/2001 | Balazs et al. | |
| 6,273,897 B1 | 8/2001 | Dalessandro et al. | |

(56) References Cited

U.S. PATENT DOCUMENTS

| | | |
|---|---|---|
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B2 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |

(56) References Cited

U.S. PATENT DOCUMENTS

| | | | |
|---|---|---|---|
| 7,909,223 | B2 | 3/2011 | Cole et al. |
| 7,913,892 | B2 | 3/2011 | Cole et al. |
| 7,918,377 | B2 | 4/2011 | Measamer et al. |
| 7,922,062 | B2 | 4/2011 | Cole et al. |
| 7,922,743 | B2 | 4/2011 | Heinrich et al. |
| 7,931,183 | B2 | 4/2011 | Orban, III |
| 7,938,307 | B2 | 5/2011 | Bettuchi |
| 7,942,302 | B2 | 5/2011 | Roby et al. |
| 7,951,166 | B2 | 5/2011 | Orban, III et al. |
| 7,959,050 | B2 | 6/2011 | Smith et al. |
| 7,967,181 | B2 | 6/2011 | Viola et al. |
| 7,975,895 | B2 | 7/2011 | Milliman |
| 8,002,795 | B2 | 8/2011 | Beetel |
| 8,006,701 | B2 | 8/2011 | Bilotti et al. |
| 8,006,889 | B2 | 8/2011 | Adams et al. |
| 8,011,551 | B2 | 9/2011 | Marczyk et al. |
| 8,011,554 | B2 | 9/2011 | Milliman |
| 8,016,177 | B2 | 9/2011 | Bettuchi et al. |
| 8,016,858 | B2 | 9/2011 | Whitman |
| 8,020,741 | B2 | 9/2011 | Cole et al. |
| 8,025,199 | B2 | 9/2011 | Whitman et al. |
| 8,028,885 | B2 | 10/2011 | Smith et al. |
| 8,038,046 | B2 | 10/2011 | Smith et al. |
| 8,043,207 | B2 | 10/2011 | Adams |
| 8,066,167 | B2 | 11/2011 | Measamer et al. |
| 8,066,169 | B2 | 11/2011 | Viola |
| 8,070,035 | B2 | 12/2011 | Holsten et al. |
| 8,070,037 | B2 | 12/2011 | Csiky |
| 8,096,458 | B2 | 1/2012 | Hessler |
| 8,109,426 | B2 | 2/2012 | Milliman et al. |
| 8,109,427 | B2 | 2/2012 | Orban, III |
| 8,113,405 | B2 | 2/2012 | Milliman |
| 8,113,406 | B2 | 2/2012 | Holsten et al. |
| 8,113,407 | B2 | 2/2012 | Holsten et al. |
| 8,123,103 | B2 | 2/2012 | Milliman |
| 8,128,645 | B2 | 3/2012 | Sonnenschein et al. |
| 8,132,703 | B2 | 3/2012 | Milliman et al. |
| 8,136,712 | B2 | 3/2012 | Zingman |
| 8,146,790 | B2 | 4/2012 | Milliman |
| 8,146,791 | B2 | 4/2012 | Bettuchi et al. |
| 8,181,838 | B2 | 5/2012 | Milliman et al. |
| 8,192,460 | B2 | 6/2012 | Orban, III et al. |
| 8,201,720 | B2 | 6/2012 | Hessler |
| 8,203,782 | B2 | 6/2012 | Brueck et al. |
| 8,211,130 | B2 | 7/2012 | Viola |
| 8,225,799 | B2 | 7/2012 | Bettuchi |
| 8,225,981 | B2 | 7/2012 | Criscuolo et al. |
| 8,231,041 | B2 | 7/2012 | Marczyk et al. |
| 8,231,042 | B2 | 7/2012 | Hessler et al. |
| 8,257,391 | B2 | 9/2012 | Orban, III et al. |
| 8,267,301 | B2 | 9/2012 | Milliman et al. |
| 8,272,552 | B2 | 9/2012 | Holsten et al. |
| 8,276,802 | B2 | 10/2012 | Kostrzewski |
| 8,281,975 | B2 | 10/2012 | Criscuolo et al. |
| 8,286,845 | B2 | 10/2012 | Perry et al. |
| 8,308,045 | B2 | 11/2012 | Bettuchi et al. |
| 8,312,885 | B2 | 11/2012 | Bettuchi et al. |
| 8,313,014 | B2 | 11/2012 | Bettuchi |
| 8,317,073 | B2 | 11/2012 | Milliman et al. |
| 8,317,074 | B2 | 11/2012 | Ortiz et al. |
| 8,322,590 | B2 | 12/2012 | Patel et al. |
| 8,328,060 | B2 | 12/2012 | Jankowski et al. |
| 8,328,062 | B2 | 12/2012 | Viola |
| 8,328,063 | B2 | 12/2012 | Milliman et al. |
| 8,343,185 | B2 | 1/2013 | Milliman et al. |
| 8,353,438 | B2 | 1/2013 | Baxter, III et al. |
| 8,353,439 | B2 | 1/2013 | Baxter, III et al. |
| 8,353,930 | B2 | 1/2013 | Heinrich et al. |
| 8,360,295 | B2 | 1/2013 | Milliman et al. |
| 8,365,974 | B2 | 2/2013 | Milliman |
| 8,403,942 | B2 | 3/2013 | Milliman et al. |
| 8,408,441 | B2 | 4/2013 | Wenchell et al. |
| 8,413,870 | B2 | 4/2013 | Pastorelli et al. |
| 8,413,872 | B2 | 4/2013 | Patel |
| 8,418,905 | B2 | 4/2013 | Milliman |
| 8,418,909 | B2 | 4/2013 | Kostrzewski |
| 8,424,535 | B2 | 4/2013 | Hessler et al. |
| 8,424,741 | B2 | 4/2013 | McGuckin, Jr. et al. |
| 8,430,291 | B2 | 4/2013 | Heinrich et al. |
| 8,430,292 | B2 | 4/2013 | Patel et al. |
| 8,453,910 | B2 | 6/2013 | Bettuchi et al. |
| 8,453,911 | B2 | 6/2013 | Milliman et al. |
| 8,485,414 | B2 | 7/2013 | Criscuolo et al. |
| 8,490,853 | B2 | 7/2013 | Criscuolo et al. |
| 8,511,533 | B2 | 8/2013 | Viola et al. |
| 8,551,138 | B2 | 10/2013 | Orban, III et al. |
| 8,567,655 | B2 | 10/2013 | Nalagatla et al. |
| 8,579,178 | B2 | 11/2013 | Holsten et al. |
| 8,590,763 | B2 | 11/2013 | Milliman |
| 8,590,764 | B2 | 11/2013 | Hartwick et al. |
| 8,608,047 | B2 | 12/2013 | Holsten et al. |
| 8,616,428 | B2 | 12/2013 | Milliman et al. |
| 8,616,429 | B2 | 12/2013 | Viola |
| 8,622,275 | B2 | 1/2014 | Baxter, III et al. |
| 8,631,993 | B2 | 1/2014 | Kostrzewski |
| 8,636,187 | B2 | 1/2014 | Hueil et al. |
| 8,640,940 | B2 | 2/2014 | Ohdaira |
| 8,662,370 | B2 | 3/2014 | Takei |
| 8,663,258 | B2 | 3/2014 | Bettuchi et al. |
| 8,672,931 | B2 | 3/2014 | Goldboss et al. |
| 8,678,264 | B2 | 3/2014 | Racenet et al. |
| 8,684,248 | B2 | 4/2014 | Milliman |
| 8,684,250 | B2 | 4/2014 | Bettuchi et al. |
| 8,684,251 | B2 | 4/2014 | Rebuffat et al. |
| 8,684,252 | B2 | 4/2014 | Patel et al. |
| 8,733,611 | B2 | 5/2014 | Milliman |
| 2003/0111507 | A1 | 6/2003 | Nunez |
| 2004/0073090 | A1 | 4/2004 | Butler et al. |
| 2004/0195289 | A1* | 10/2004 | Aranyi ............... A61B 17/115 227/180.1 |
| 2005/0051597 | A1 | 3/2005 | Toledano |
| 2005/0107813 | A1 | 5/2005 | Gilete Garcia |
| 2006/0000869 | A1 | 1/2006 | Fontayne |
| 2006/0011698 | A1 | 1/2006 | Okada et al. |
| 2006/0201989 | A1 | 9/2006 | Ojeda |
| 2007/0027473 | A1 | 2/2007 | Vresh et al. |
| 2007/0029363 | A1 | 2/2007 | Popov |
| 2007/0060952 | A1 | 3/2007 | Roby et al. |
| 2009/0236392 | A1 | 9/2009 | Cole et al. |
| 2009/0236398 | A1 | 9/2009 | Cole et al. |
| 2009/0236401 | A1 | 9/2009 | Cole et al. |
| 2010/0019016 | A1 | 1/2010 | Edoga et al. |
| 2010/0038401 | A1* | 2/2010 | Milliman ............ A61B 17/1114 227/175.1 |
| 2010/0051668 | A1 | 3/2010 | Milliman et al. |
| 2010/0084453 | A1 | 4/2010 | Hu |
| 2010/0147923 | A1 | 6/2010 | D'Agostino et al. |
| 2010/0163598 | A1 | 7/2010 | Belzer |
| 2010/0224668 | A1 | 9/2010 | Fontayne et al. |
| 2010/0230465 | A1 | 9/2010 | Smith et al. |
| 2010/0258611 | A1 | 10/2010 | Smith et al. |
| 2010/0264195 | A1 | 10/2010 | Bettuchi |
| 2010/0327041 | A1 | 12/2010 | Milliman et al. |
| 2011/0011916 | A1 | 1/2011 | Levine |
| 2011/0114697 | A1 | 5/2011 | Baxter, III et al. |
| 2011/0114700 | A1 | 5/2011 | Baxter, III et al. |
| 2011/0144640 | A1 | 6/2011 | Heinrich et al. |
| 2011/0147432 | A1 | 6/2011 | Heinrich et al. |
| 2011/0192882 | A1 | 8/2011 | Hess et al. |
| 2012/0145755 | A1 | 6/2012 | Kahn |
| 2012/0193395 | A1 | 8/2012 | Pastorelli et al. |
| 2012/0193398 | A1 | 8/2012 | Williams et al. |
| 2012/0232339 | A1 | 9/2012 | Csiky |
| 2012/0273548 | A1 | 11/2012 | Ma et al. |
| 2012/0292366 | A1* | 11/2012 | Nalagatla ......... A61B 17/07292 227/175.1 |
| 2012/0292371 | A1* | 11/2012 | Nalagatla ........... A61B 17/1155 227/179.1 |
| 2012/0325888 | A1 | 12/2012 | Qiao et al. |
| 2013/0015232 | A1 | 1/2013 | Smith et al. |
| 2013/0020372 | A1 | 1/2013 | Jankowski et al. |
| 2013/0020373 | A1 | 1/2013 | Smith et al. |
| 2013/0032628 | A1 | 2/2013 | Li et al. |
| 2013/0056516 | A1 | 3/2013 | Viola |

(56) References Cited

U.S. PATENT DOCUMENTS

| | | |
|---|---|---|
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2015/0069108 A1* | 3/2015 | Williams ........... A61B 17/1155 227/175.1 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0258471 A1* | 9/2017 | DiNardo .............. A61B 17/072 |
| 2017/0281171 A1* | 10/2017 | Shelton, IV ....... A61B 17/3211 |
| 2018/0242973 A1* | 8/2018 | Guerrera .......... A61B 17/07207 |
| 2018/0242974 A1* | 8/2018 | Guerrera ........... A61B 17/1155 |
| 2019/0059901 A1* | 2/2019 | Guerrera .......... A61B 17/00234 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 0536882 A2 | 4/1993 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

\* cited by examiner

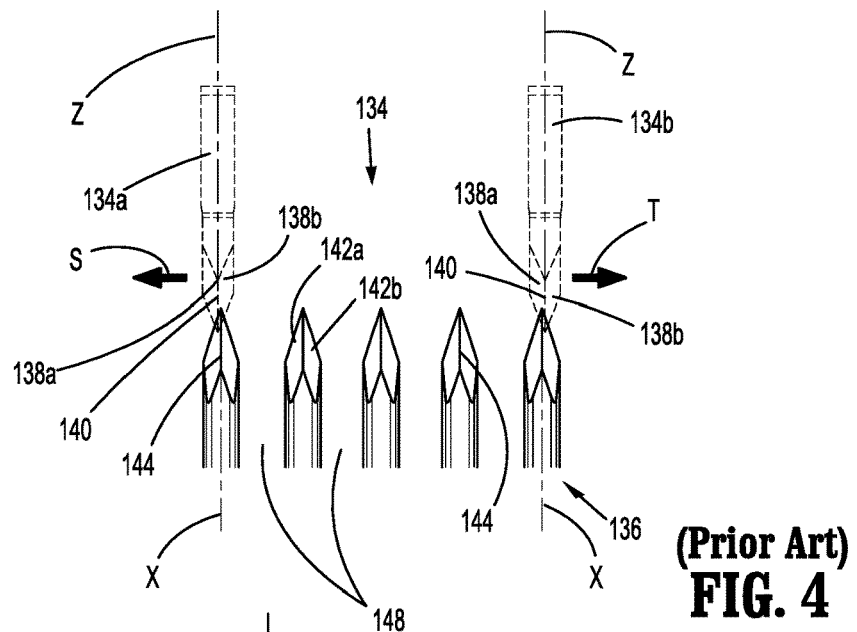
(Prior Art)
FIG. 4
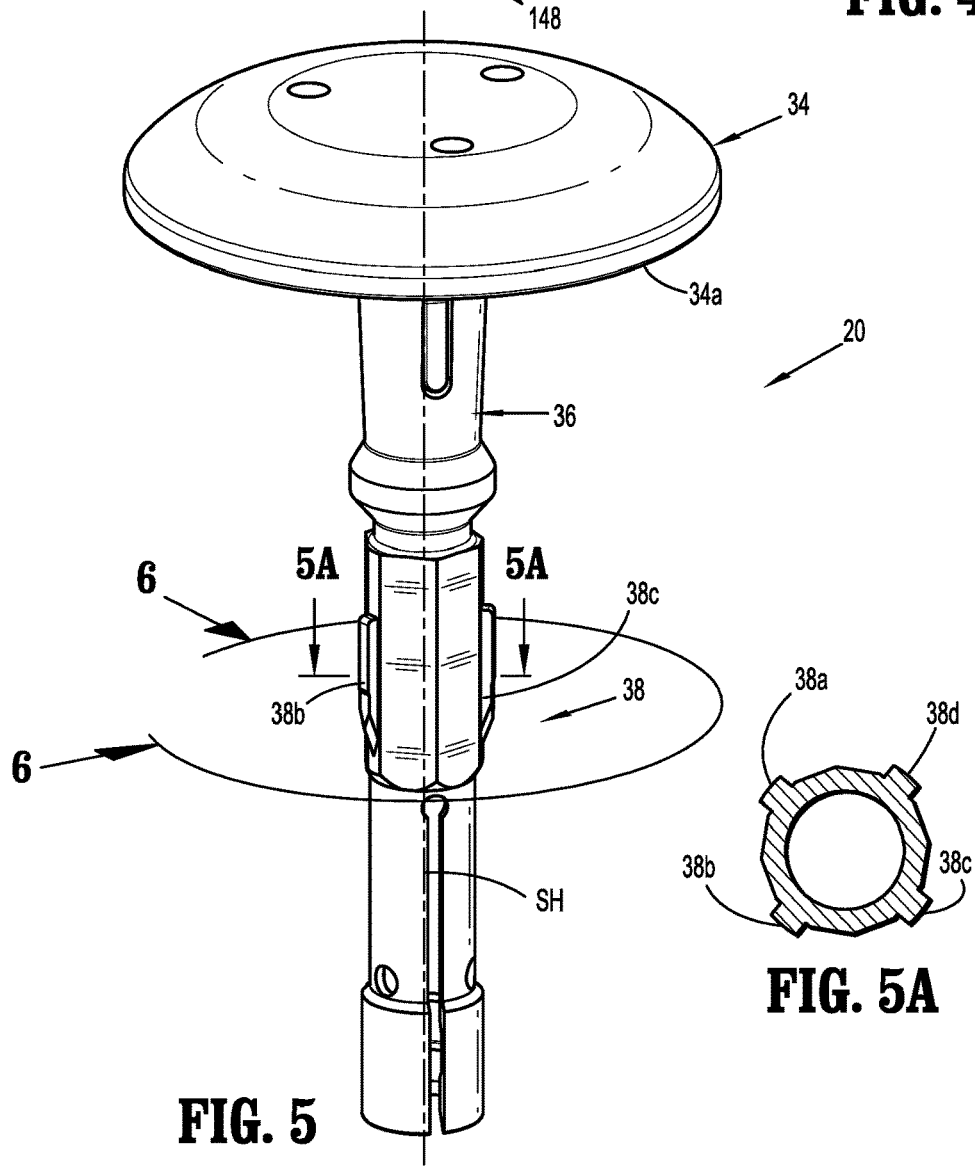
FIG. 5
FIG. 5A

CIRCULAR STAPLING DEVICE WITH A-FRAME SPLINES

BACKGROUND

1. Technical Description

The present disclosure is directed to circular stapling devices, and more particularly, to circular stapling devices including splines having an A-frame structure to prevent malformation of staples due to spline crashing.

2. Background of Related Art

Circular stapling devices are utilized by clinicians to apply one or more surgical fasteners, e.g., staples or two-part fasteners, to body tissue for the purpose of joining segments of body tissue together and/or for the creation of an anastomosis. Circular stapling devices generally include a shell assembly including a staple cartridge supporting a plurality of annular rows of staples and an anvil assembly operatively associated with the shell assembly and having annular arrays of staple receiving pockets. The staple receiving pockets are aligned with the annular rows of staples to provide a surface against which the plurality of annular rows of staples can be formed.

During a typical tissue fastening procedure, the anvil assembly of the stapling device is positioned within one segment of body tissue and the shell assembly is positioned in an adjacent segment of body tissue. The anvil assembly is then attached to the body portion of the stapling device and the stapling device is actuated to move the anvil assembly in relation to the staple cartridge of the shell assembly to clamp the body tissue segments together.

Typically, the anvil assembly includes an anvil shaft that includes splines that mate with splines formed within a shell housing of the shell assembly to align the staple forming pockets of the anvil assembly with staple receiving pockets of the staple cartridge of the shell assembly. The splines on the anvil shaft and on the shell housing of the shell assembly include left and right tapered ends that define an apex. When the tapered ends of the splines of the anvil assembly engage the tapered ends of the shell assembly, the anvil assembly is cammed into rotation to align the staple forming pockets of the anvil assembly with staple receiving pockets of the staple cartridge of the shell assembly. However, if the apexes of the splines of the anvil assembly and the shell assembly engage head on, i.e., crash, the splines of the anvil assembly and the shell assembly may be damaged such that proper alignment of the anvil and shell assemblies is prevented such that malformation of the staples may occur during firing of the stapling device.

A continuing need exists for a circular stapling device having a more reliable alignment structure for aligning the staple forming pockets of the anvil assembly with the staple receiving pockets of the staple cartridge of the shell assembly to minimize the occurrence of staple malformation.

SUMMARY

One aspect of the disclosure is directed to a surgical stapling device including an approximation assembly, an anvil assembly, and a shell assembly. The approximation assembly includes an anvil retainer. The anvil assembly includes an anvil shaft having at least one anvil spline and an anvil head having an anvil surface defining a plurality of staple deforming recesses. The anvil head is supported on a distal portion of the anvil shaft. The shell assembly includes a shell housing having an inner housing portion defining a bore. A plurality of shell splines are supported on the inner housing portion within the bore. Each of the plurality of shell splines has spaced side walls and a pair of tapered surfaces extending from the spaced side walls that intersect at an apex. Each of the spaced side walls of adjacent shell splines of the plurality of shell splines defines a primary channel and the spaced side walls of each of the plurality of shell splines defines a secondary channel. The secondary channels are positioned proximally of and in axial alignment with the apex of the respective shell spline. The primary and secondary channels are dimensioned to receive one of the at least one anvil splines.

Another aspect of the disclosure is directed to a shell assembly for a circular stapling device including a shell housing having an inner housing portion defining a bore, and a plurality of shell splines supported on the inner housing portion within the bore. Each of the plurality of shell splines has spaced side walls and a pair of tapered surfaces that intersect at an apex and extend distally from the spaced side walls. Each of the spaced side walls of adjacent shell splines of the plurality of shell splines defines a primary channel and the spaced side walls of each of the plurality of shell splines defines a secondary channel that is positioned proximally of and in axial alignment with the apex of the respective shell spline. The primary and secondary channels are dimensioned to receive an anvil spline of a surgical stapling device.

Another aspect of the present disclosure is directed to a tool assembly for a surgical stapling device including an anvil assembly and a shell assembly. The anvil assembly includes an anvil shaft having at least one anvil spline and an anvil head having an anvil surface defining a plurality of staple deforming recesses. The anvil head is supported on a distal portion of the anvil shaft. The shell assembly includes a shell housing having an inner housing portion defining a bore. A plurality of shell splines are supported on the inner housing portion within the bore. Each of the plurality of shell splines has spaced side walls and a pair of tapered surfaces extending from the spaced side walls that intersect at an apex. Each of the spaced side walls of adjacent shell splines of the plurality of shell splines defines a primary channel and the spaced side walls of each of the plurality of shell splines defines a secondary channel. The secondary channels are positioned proximally of and in axial alignment with the apex of the respective shell spline. The primary and secondary channels are dimensioned to receive one of the at least one anvil splines.

In embodiments, the tapered surfaces of each of the shell splines are positioned on a distal portion of the shell spline.

In some embodiments, the at least one anvil spline includes a pair of tapered surfaces that intersect at an apex.

In certain embodiments, the primary and secondary channels are positioned to receive the at least one anvil spline to properly align the anvil assembly with the shell assembly.

In embodiments, the apex of each of the shell splines is constructed to fracture upon engagement with the apex of the at least one anvil spline to allow passage of the at least one anvil spline into a respective one of the secondary channels.

In some embodiments, the at least one anvil spline includes a plurality of anvil splines.

In certain embodiments, the tapered surfaces of each of the plurality of shell splines is configured to cam the at least one anvil spline into a respective primary channel when the apex of the at least one anvil spline engages one of the tapered surfaces.

In embodiments, the shell assembly includes a staple cartridge supported within the shell housing.

BRIEF DESCRIPTION OF THE DRAWINGS

Various embodiments of the presently disclosed circular stapling device are described herein below with reference to the drawings, wherein:

FIG. 4 is a schematic view of a spline configuration of the anvil assembly of the "Prior Art" surgical stapling device shown in FIG. 3;

FIG. 5 is a side perspective view of the anvil assembly of the surgical stapling device shown in FIG. 1;

FIG. 5A is a cross-sectional view taken along section line 5A-5A of FIG. 5;

DETAILED DESCRIPTION OF EMBODIMENTS

Figure 1:
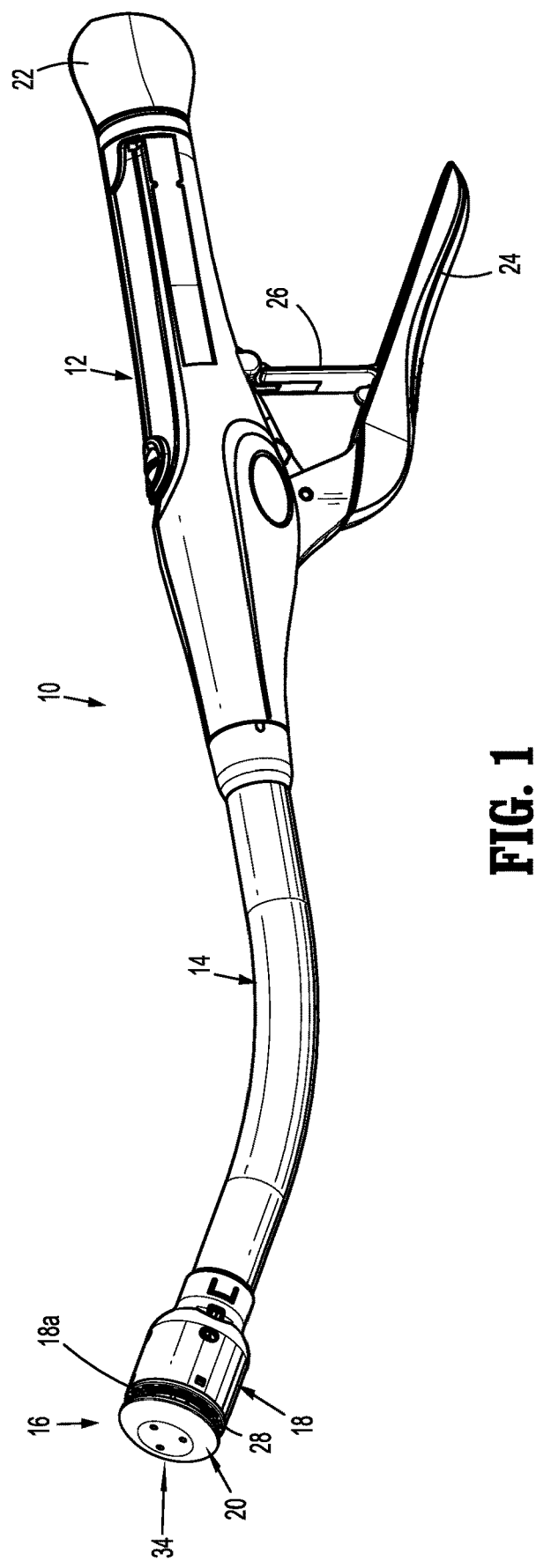
FIG. 1 is a side perspective view of an exemplary embodiment of the presently disclosed surgical stapling device with a tool assembly in a clamped position.

The presently disclosed stapling device will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

The presently disclosed surgical stapling device includes an anvil assembly and a shell assembly. The shell assembly includes splines having an A-frame configuration that are supported on a shell housing of the shell assembly of the surgical stapling device. The A-frame splines include a triangular tip that defines an apex. The triangular tip is positioned to engage splines on a center rod of the anvil assembly to properly align the anvil assembly with the shell assembly. The A-frame splines are spaced from each other to define primary channels that are dimensioned to receive the splines on the center rod of the anvil assembly to properly align the anvil assembly with the shell assembly. The A-frame splines also define secondary channels that are positioned proximally of the apex of the A-frame splines. In situations in which an apex of the splines on center rod of the anvil assembly "crash" into the apex of the A-frame splines of the shell assembly, i.e., the apexes of the splines meet head on, the A-frame splines of the shell assembly are constructed to fracture to allow the splines of the anvil center rod of the anvil assembly to penetrate into the A-frame splines and pass into the secondary channels of the A-frame splines to properly align the anvil assembly with the shell assembly of the stapling device. The inclusion of A-frame splines having secondary channels on the shell assembly reduces the likelihood of staple malformation when the splines "crash".

Figure 2:
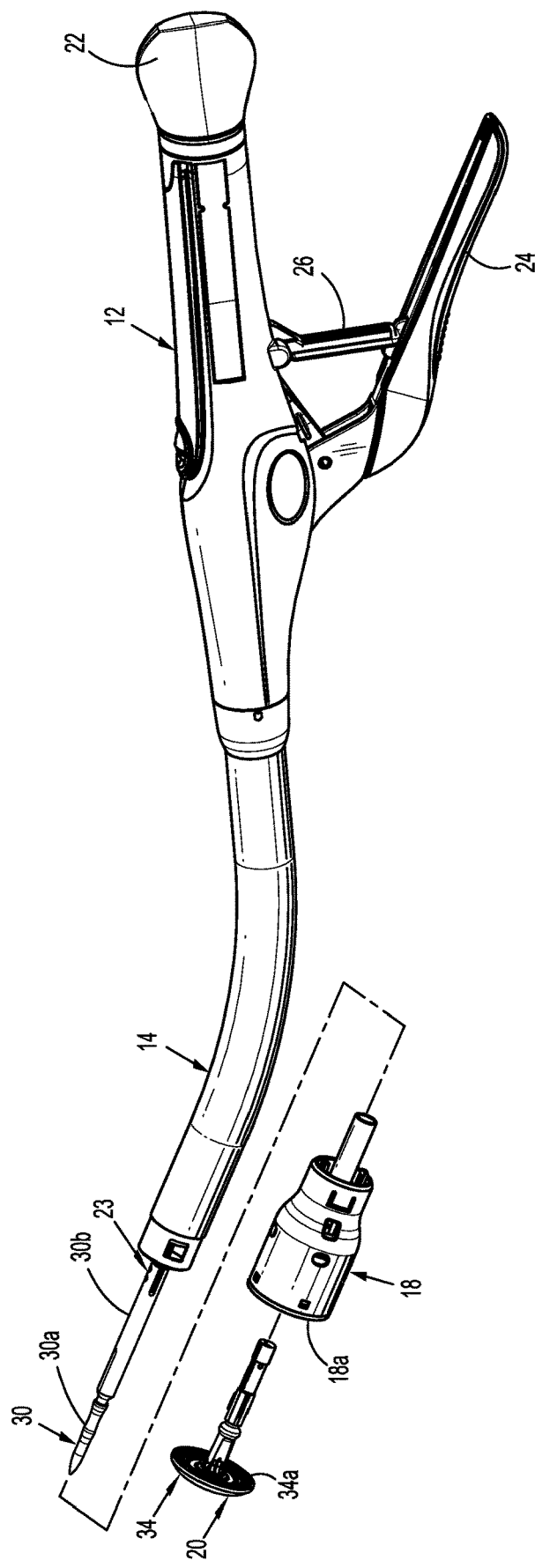
FIG. 2 is a side perspective view of the surgical stapling device shown in FIG. 1 with shell and anvil assemblies of the tool assembly separated from the remaining portion of the stapling device.

Referring to FIGS. 1 and 2, the presently disclosed surgical stapling device shown generally as stapling device 10 includes a handle assembly 12, an elongate body portion 14 that extends distally from the handle assembly 12, and a tool assembly 16 that is supported on a distal portion of the elongate body portion 14. The tool assembly 16 includes a shell assembly 18 that supports a staple cartridge 18a and an anvil assembly 20 that includes an anvil head 34 having an anvil surface 34a that defines a plurality of staple deforming recesses (FIG. 2.) The handle assembly 12 includes an approximation knob 22 of an approximation assembly 23 that is operable to move the anvil assembly 20 between unclamped and clamped positions in relation to the cartridge assembly 18, a firing trigger 24 that that operates a firing mechanism (not shown) to fire staples (not shown) from the staple cartridge 18a into tissue, and a firing trigger lockout 26 that is pivotally supported on the handle assembly 12 and is positioned to prevent inadvertent firing of the stapling device 10. For a detailed description of an exemplary circular stapling device including known approximation, firing, and lockout mechanisms, see U.S. Pat. No. 7,857,187 ("the '187 Patent") which is incorporated herein by reference in its entirety.

Although the presently disclosed stapling device 10 is shown and described as being a manually powered device, it is envisioned that the stapling device 10 can also be an electrically powered device such as described in U.S. Patent Publication No. 2015/0048140 which is incorporated herein by reference in its entirety.

The staple cartridge 18a of the shell assembly 18 and the anvil surface 34a (FIG. 2) of the anvil assembly 20 have an annular configuration. The anvil assembly 20 is movable in relation to the shell assembly 18 between a spaced position and a clamped position to move the anvil surface 34a into juxtaposed alignment with the staple cartridge 18a. The staple cartridge 18a defines staple receiving slots 28 (FIG. 1) that are aligned with the staple deforming recesses of the anvil surface 34a when the staple cartridge 18a and the anvil surface 34a are properly aligned such that staples ejected from the staple receiving slots 28 are deformed within the staple deforming recesses when the stapling device 10 is fired.

The anvil assembly 20 is releasably supported on an anvil retainer 30 (FIG. 2) of the stapling device 10. The anvil retainer 30 forms part of an approximation mechanism of the stapling device 10 and includes a distal portion 30a and a proximal portion 30b (FIG. 2). The distal portion 30a of the anvil retainer 30 extends from a distal end of the elongate body portion 14 of the stapling device 10 and through the shell assembly 18 to a position to engage the anvil assembly 20. The proximal portion 30b of the anvil retainer 30 is operatively connected to the approximation knob 22 such that rotation of the approximation knob 22 causes the anvil retainer 30 to move within the shell assembly 18 to move the anvil assembly 20 in relation to the staple cartridge 18a between the spaced position and the clamped position.

The shell assembly 18 includes an annular knife (not shown) that is movable from a retracted position to an advanced position within the shell assembly 18 during firing of the stapling device 10 to transect tissue clamped between the staple cartridge 18a and the anvil surface 34a. (See the '187 Patent.) In some embodiments, the shell assembly 18 is releasably coupled to a distal portion of the elongate body 14 of the stapling device 10 to facilitate replacement of the shell assembly 18 after each firing of the stapling device 10. Mechanisms for releasably coupling the shell assembly 18 to the elongate body portion 14 of the stapling device 10 are described in U.S. Patent Publication Nos. 2016/0310141, 2016/0192938, and 2016/0192934 which are incorporated herein in their entirety by reference. Alternately, the shell assembly 18 can be fixedly secured to the distal portion of the elongate body 14.

Figure 3:
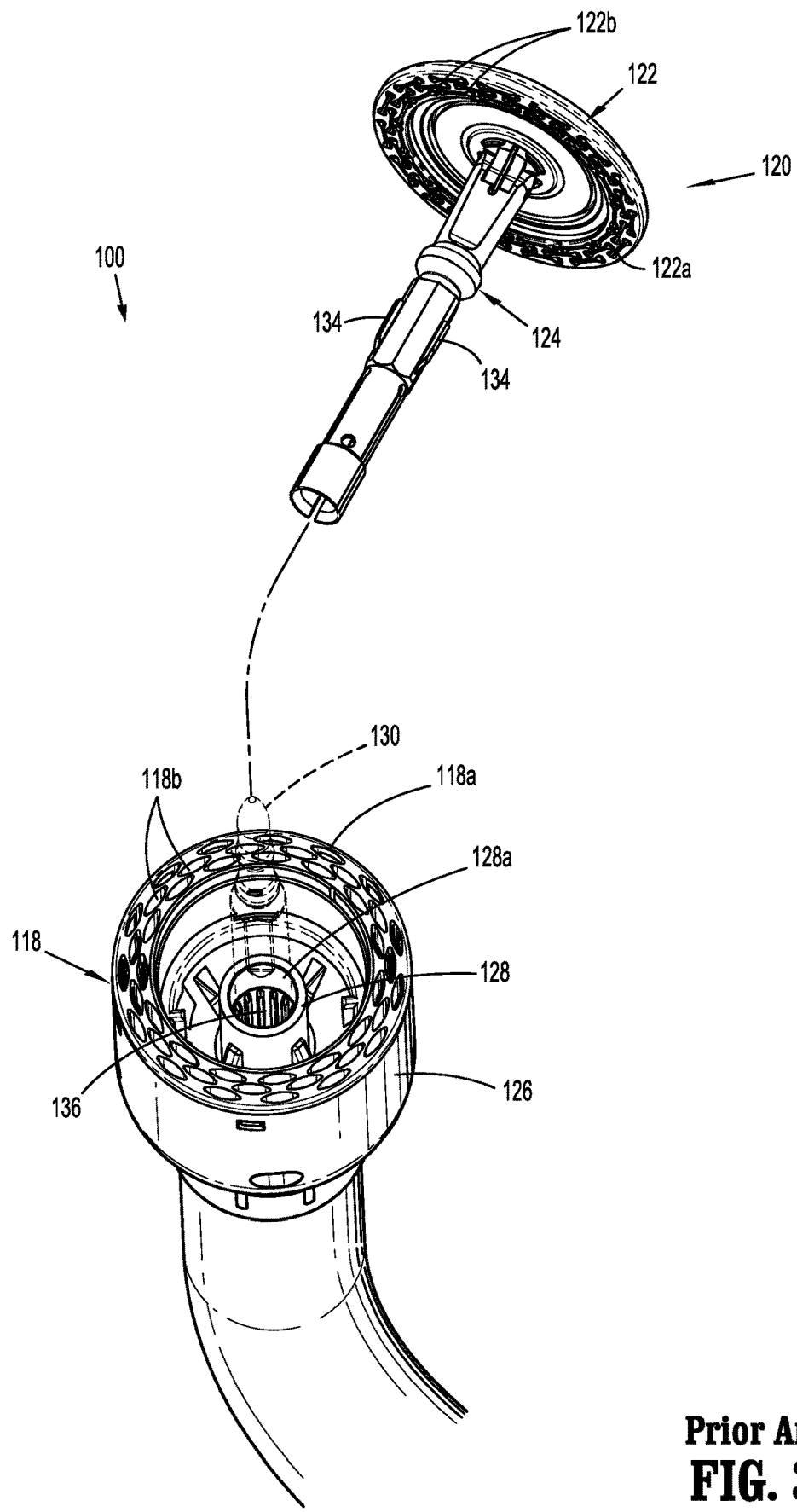
FIG. 3 is a perspective view from a distal end of a "Prior Art" surgical stapling device with the anvil assembly of the tool assembly of the surgical stapling device separated from an anvil retainer (shown in phantom) of the surgical stapling device.

Referring to FIG. 3, prior art circular stapling devices 100 include an anvil assembly 120 having an anvil head 122 and an anvil shaft or center rod 124, and a shell assembly 118 having a staple cartridge 118a and a shell housing 126 having an inner housing portion 128 that defines a through bore 128a. The anvil head 122 defines an anvil surface 122a that defines annular arrays of staple deforming recesses 122b and the staple cartridge 118a defines an annular array of staple receiving slots 118b. An anvil retainer 130 (shown in phantom) includes a distal end that is configured to releasably engage the anvil shaft 124 of the anvil assembly 120. The anvil retainer 130 is received within the through bore 128a of the shell housing 126 and is movable between retracted and advanced positions. When the anvil shaft 124 is coupled to the anvil retainer 130 and the anvil retainer 130 is retracted (via actuation of the approximation knob 22, FIG. 1), the anvil shaft 124 is drawn into the through bore 128a of the inner housing portion 128 of the shell housing 126.

In order to align the staple deforming recesses 122b of the anvil surface 122a of the anvil assembly 120 with the staple receiving slots 118b of the staple cartridge 118a of the shell assembly 118, the anvil shaft 124 includes a plurality of splines 134 including adjacent splines 134a, 134b (FIG. 4) that are received in channels 148 defined between splines 136 formed along an inner wall of the inner housing portion 128 of the shell housing 126. Each of the splines 134 of the anvil assembly 120 defines a central axis "Z" and left and right tapered cam surfaces 138a, 138b positioned on opposite sides of the central axis "Z" as viewed in FIG. 4. The tapered surfaces 138a, 138b meet at their proximal ends at an apex 140. Similarly, each of the splines 136 of the shell assembly 118 defines a central axis "X" and left and right tapered cam surfaces 142a, 142b positioned on opposite sides of the central axis "X". The tapered surfaces 142a, 142b meet at their distal ends at an apex 144.

When the anvil assembly 120 is attached to the anvil retainer 130 (FIG. 3) and the anvil retainer 130 and anvil assembly 120 are retracted into the through bore 128a (FIG. 3) of the inner housing portion 128 of the shell housing 126, the splines 134 of the anvil assembly 120 move towards the splines 136 of the shell assembly 118. If the splines 134 of the anvil assembly 120 are misaligned with channels 148 defined between the splines 136 of the shell assembly 118, the apexes 140 of the anvil splines 134a, 134b will engage one of the cam surfaces 142a, 142b of the splines 136. When the apexes 140 of the splines 134a, 134b (only two are shown) engage the left tapered cam surface 142a of the splines 136, the engagement urges or cams the anvil assembly 120 to rotate in the direction indicated by arrow "S" to realign the splines 134a, 134b so that they enter into the channels 148 defined between the splines 136 of the shell assembly 118. However, if the apexes 140 of the splines 134a-b of the anvil assembly 120 are aligned with the apexes 144 of the splines 136 of the shell assembly 118 such that the apexes 140 and 144 meet head on or "crash", the apexes 140 and 144 may be damaged to that extent that the anvil assembly 120 is not rotated into alignment with the shell assembly 118. When this occurs, alignment between the staple receiving slots 118b of the staple cartridge 118a may not be properly aligned with the staple deforming recesses 122b of the anvil assembly 120 when the staples are fired. This may result staple malformation.

Figure 6:
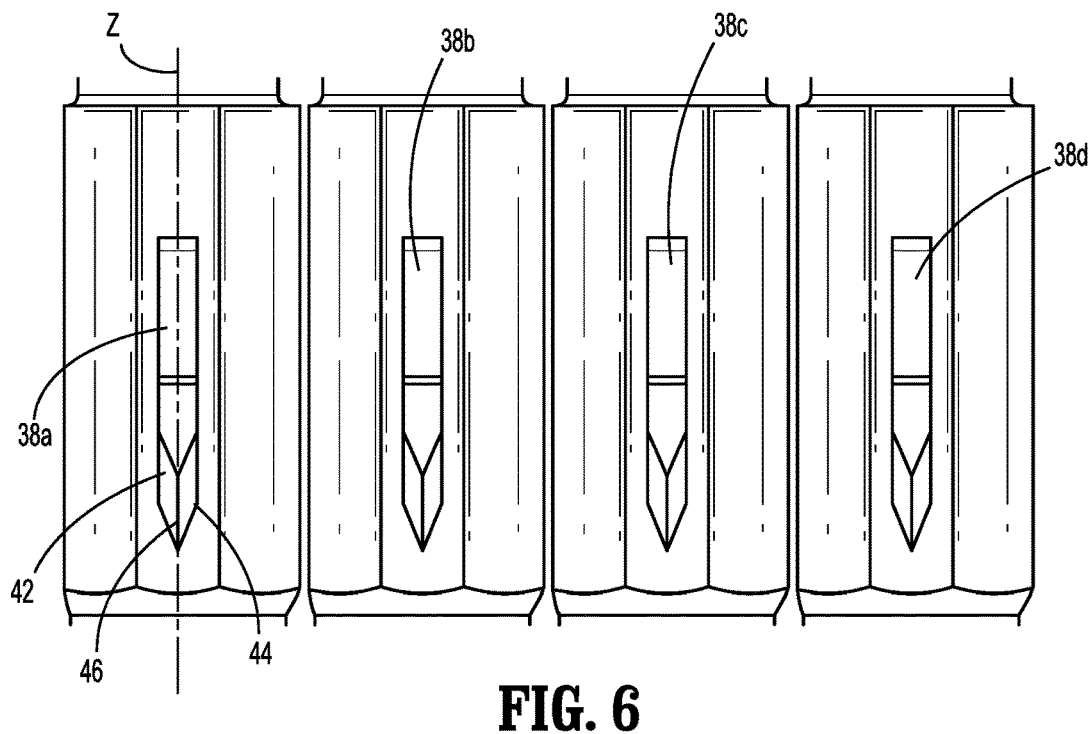
FIG. 6 is a side view taken in the direction indicated by arrows 6-6 of FIG. 5.
Figure 7:
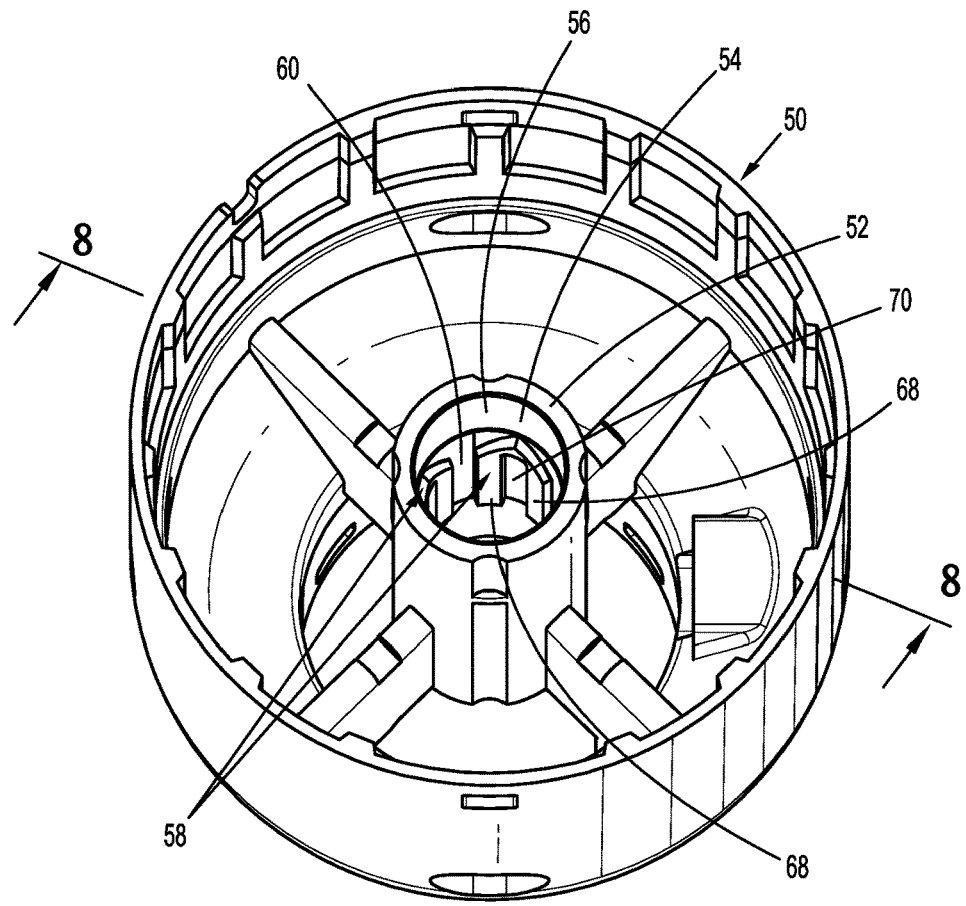
FIG. 7 is a perspective view from the distal end of the shell housing of the shell assembly of the surgical stapling device shown in FIG. 1.
Figure 8:
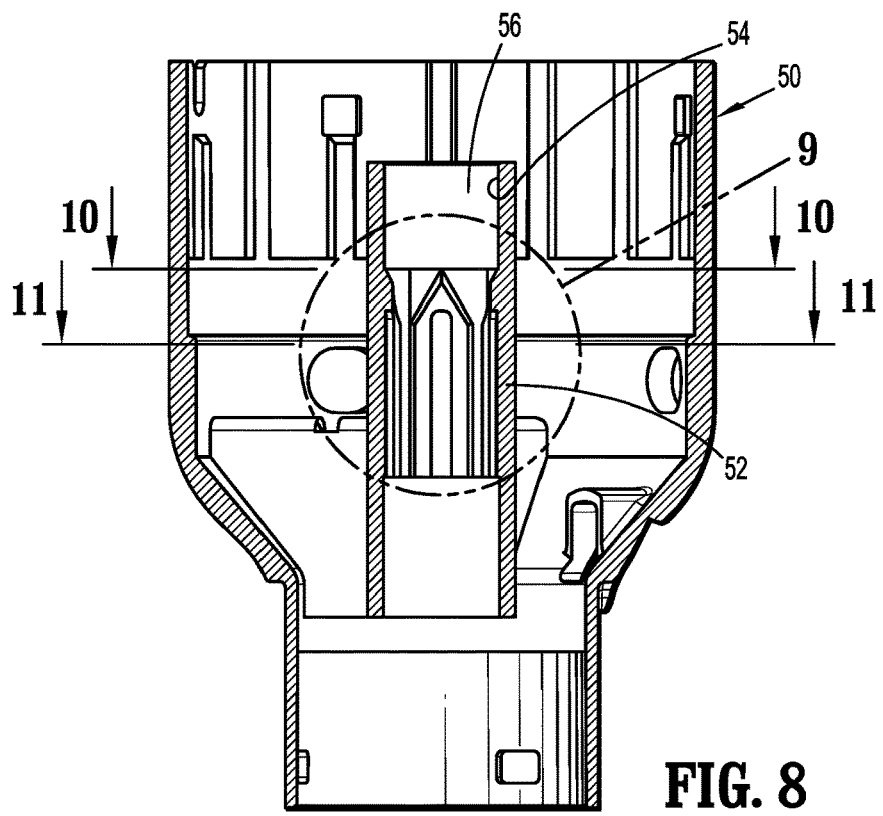
FIG. 8 is a cross-sectional view taken along section line 8-8 of FIG. 7.

Referring to FIGS. 5-6, in the presently disclosed surgical stapling device 10 (FIG. 1), the anvil assembly 20 includes an anvil head assembly 34 which includes the anvil surface 34a defining a plurality of staple deforming recesses similar to recesses 122b of FIG. 3 and an anvil shaft 36 that defines a longitudinal axis "SH" (FIG. 5). The anvil shaft 36 supports at least one spline 38 positioned on the anvil shaft 36. In some embodiments, the at least one spline 38 includes a first spline 38a, a second spline 38b, a third spline 38c, and a fourth spline 38d. Alternately, the at least one spline 38 may include one or more splines, e.g., 2 or 3. Each of the splines 38a-d (FIG. 5A) defines a longitudinal axis "Z"

(FIG. 6) that extends in a direction that is substantially parallel to the longitudinal axis "SH" (FIG. 5) of the anvil shaft 36 and includes left and right tapered cam surfaces 42 and 44 (as viewed in FIG. 6), respectively, that meet to define an apex 46 positioned at a proximal end of the respective spline 38a-d.

Figure 9:
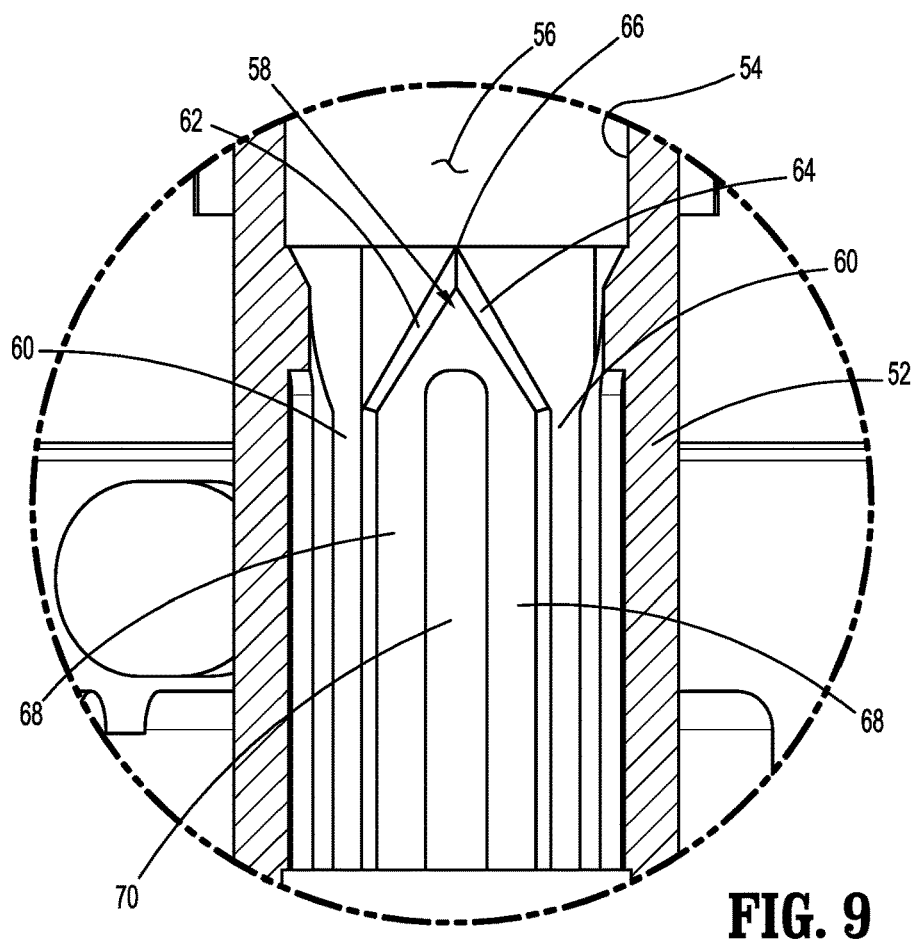
FIG. 9 is an enlarged view of the indicated area of detail shown in FIG. 8.
Figure 10:
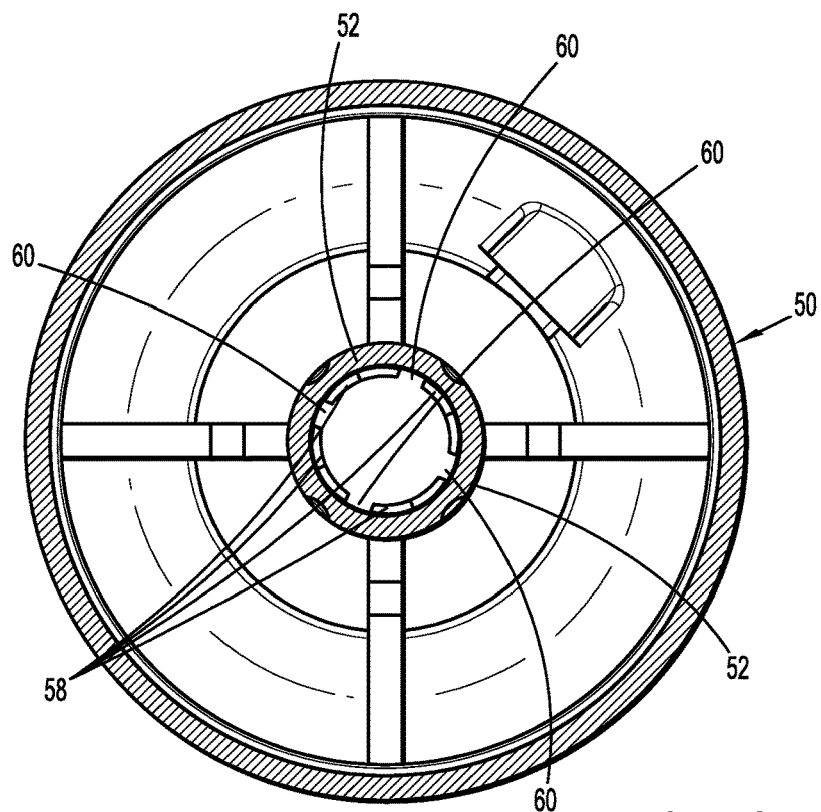
FIG. 10 is a cross-sectional view taken along section line 10-10 of FIG. 8.
Figure 11:
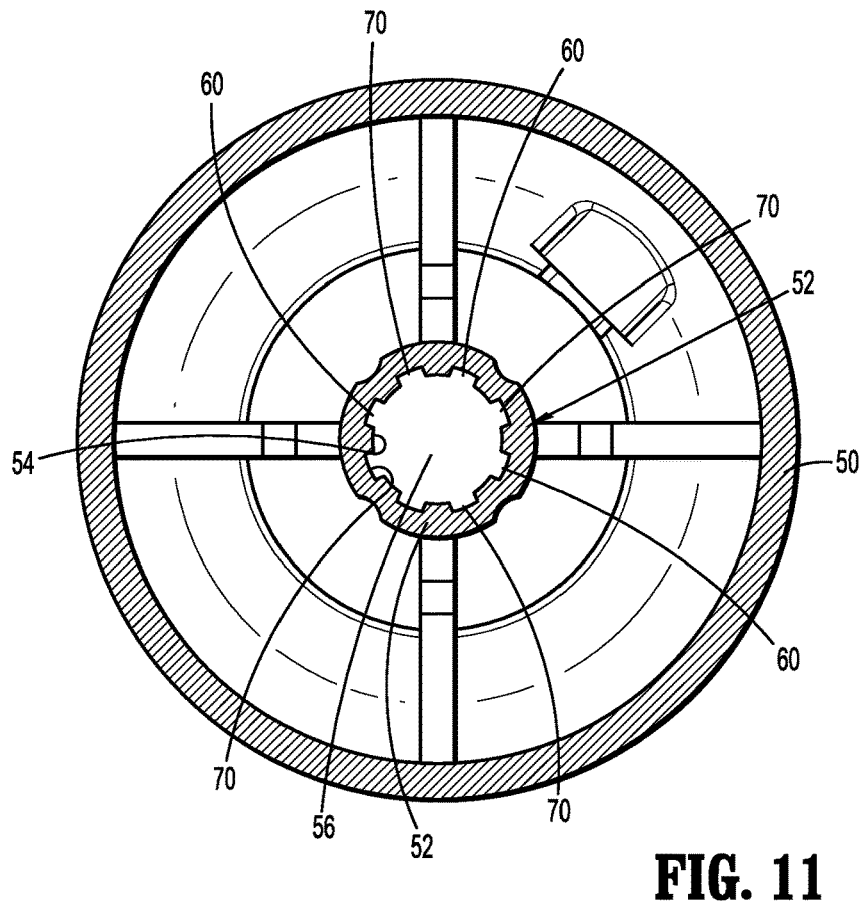
FIG. 11 is a cross-sectional view taken along section line 11-11 of FIG. 8.
Figure 12:
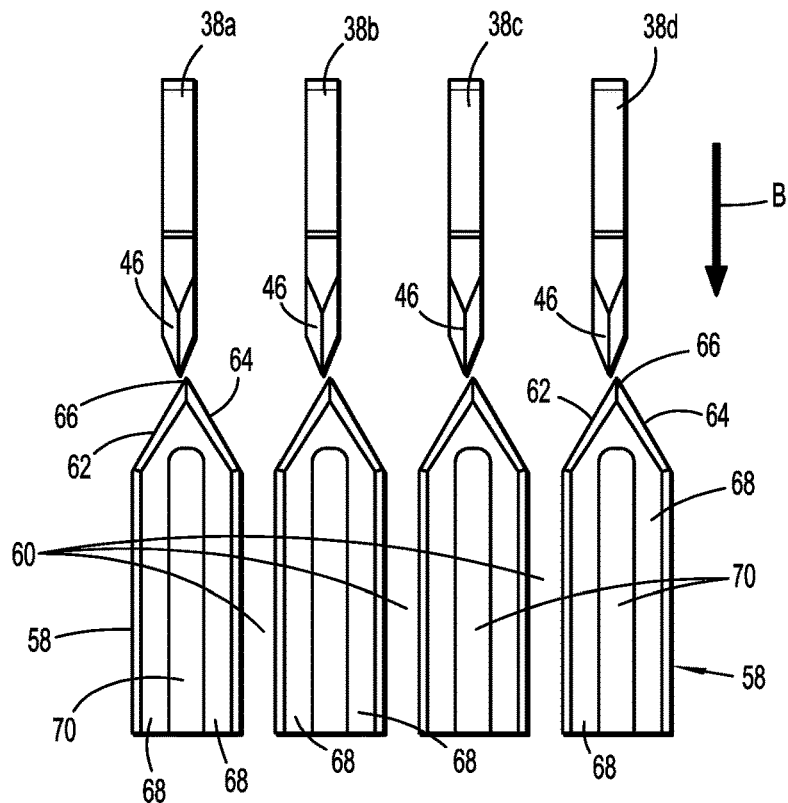
FIG. 12 is a schematic view of splines of the anvil assembly of the surgical stapling device shown in FIG. 1 and the splines of the shell assembly of the surgical stapling device shown in FIG. 1 prior to engagement of the splines with each other.

Referring to FIGS. 7-11, the shell assembly 18 (FIG. 1) includes a shell housing 50 having an inner housing portion 52. The inner housing portion 52 includes an inner surface 54 that defines an inner bore 56. The inner surface 54 includes a plurality of spaced A-frame splines 58. Each of the A-frame splines 58 defines a primary channel 60 with each adjacent A-frame spline 58. Each of the A-frame splines 58 includes left and right cam surfaces 62 and 64 respectively as viewed in FIG. 9, an apex 66 and side walls 68. The side walls 68 define secondary channels 70 that are positioned proximally of (or beneath as viewed in FIG. 9) the apex 66 of a respective A-frame spline 58. As illustrated in FIG. 9, each of the secondary channels defines a longitudinal axis that extends through an apex 66 of an A-frame spline 58.

As discussed above in regard to the stapling device 100 shown in FIG. 3, the inner bore 56 of the inner housing portion 52 of the shell housing 50 receives the anvil retainer 30 of the stapling device 10. When the anvil shaft 36 (FIG. 5) of the anvil assembly 20 is secured to the anvil retainer 30 and the anvil assembly 20 is moved to the clamped position, the anvil retainer 30 and the anvil shaft 36 of the anvil assembly 20 are retracted into the inner bore 56 of the shell housing 50. As the anvil shaft 36 (FIG. 5) is drawn into the inner bore 56 of the shell housing 50, the splines 38a-d of the anvil shaft 36 approach and subsequently engage the A-frame splines 58 of the shell housing 50.

Figure 13:
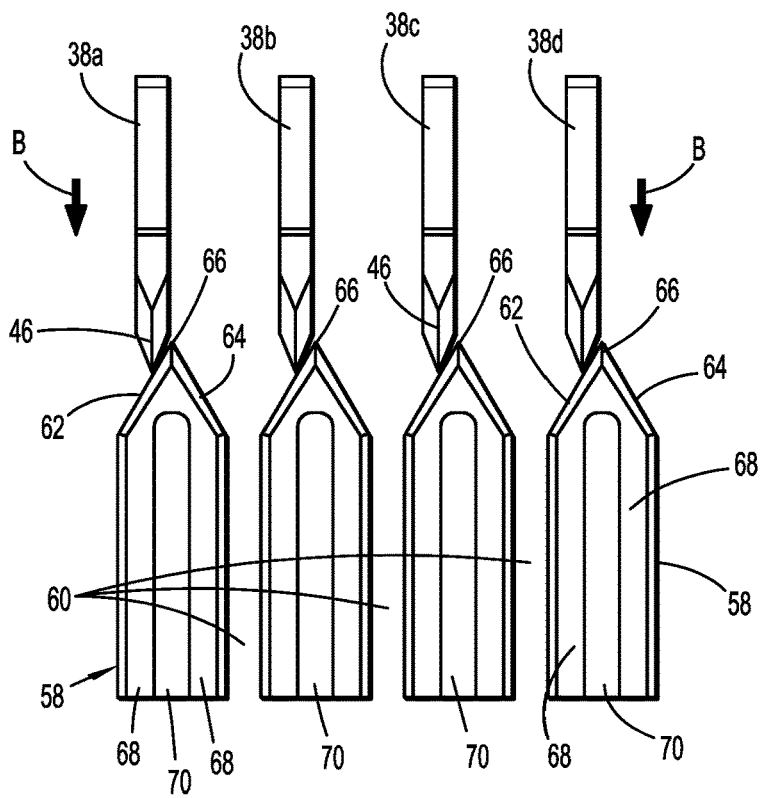
FIG. 13 is a schematic view of the splines of the anvil assembly and the splines of the shell assembly shown in FIG. 12 immediately after engagement of the splines with each other.
Figure 14:
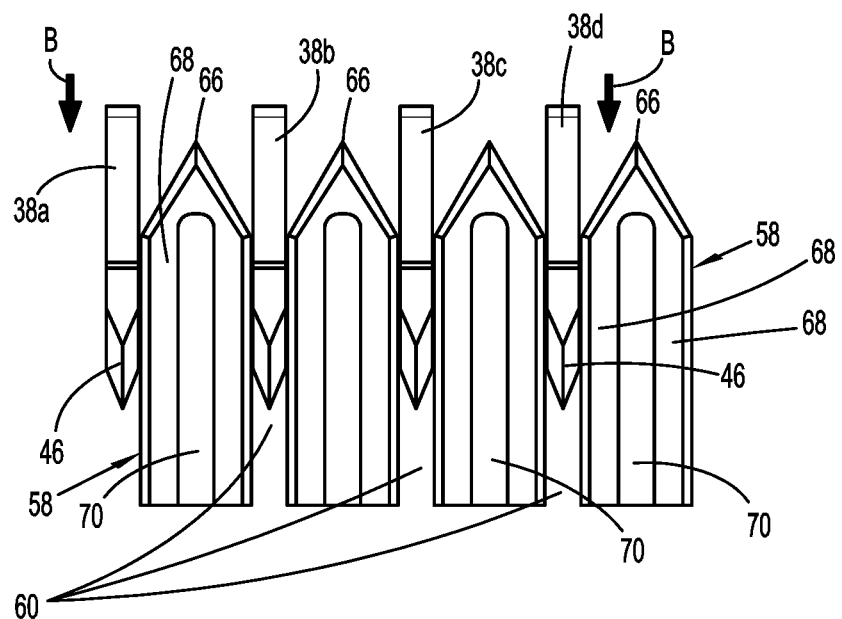
FIG. 14 is a schematic view of the splines of the anvil assembly and the splines of the shell assembly shown in FIG. 13 after the anvil assembly has rotated into alignment with the shell assembly and the splines of the anvil assembly have moved into the primary channels of the shell assembly.
Figure 15:
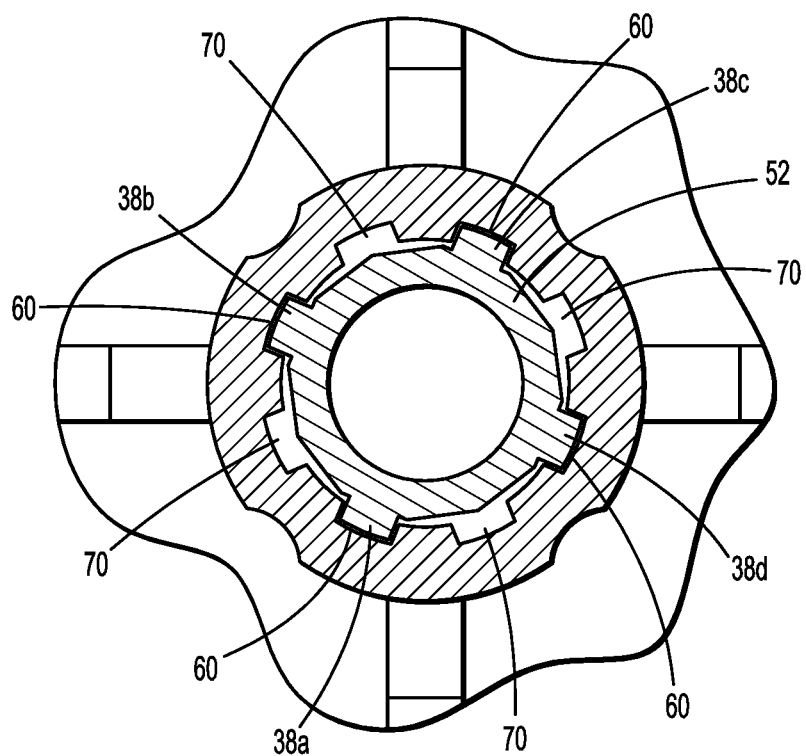
FIG. 15 is cross-sectional view taken through the splines of the anvil and shell assemblies as the splines of the anvil assembly move into the primary channels of the shell assembly.

Referring to FIGS. 12-15, as the anvil shaft 36 is drawn into the inner bore 56 of the shell housing 50 in the direction indicated by arrow "B" in FIG. 13, if the apex 46 of the splines 38a-d are positioned to engage one of the cam surfaces 62 and 64 of the A-frame splines 58 (FIG. 12), the apex 46 of the splines 38a-d will be cammed along the cam surfaces 62 or 64 of the A-frame splines 58 (FIG. 13) such that the anvil assembly 20 will rotate in relation to the shell assembly 18 and the splines 38a-d will be directed into the respective primary channels 60 defined between adjacent A-frame splines 58 (FIG. 14). This rotational movement of the anvil assembly 20 in relation to the shell assembly 18 moves the staple receiving slots 28 (FIG. 1) of the staple cartridge 18a into alignment with the staple deforming recesses of the anvil surface 34a such that staples ejected from the staple receiving slots 28 will be properly deformed within the staple deforming recesses on the anvil surface 34a when the stapling device 10 is fired.

Figure 16:
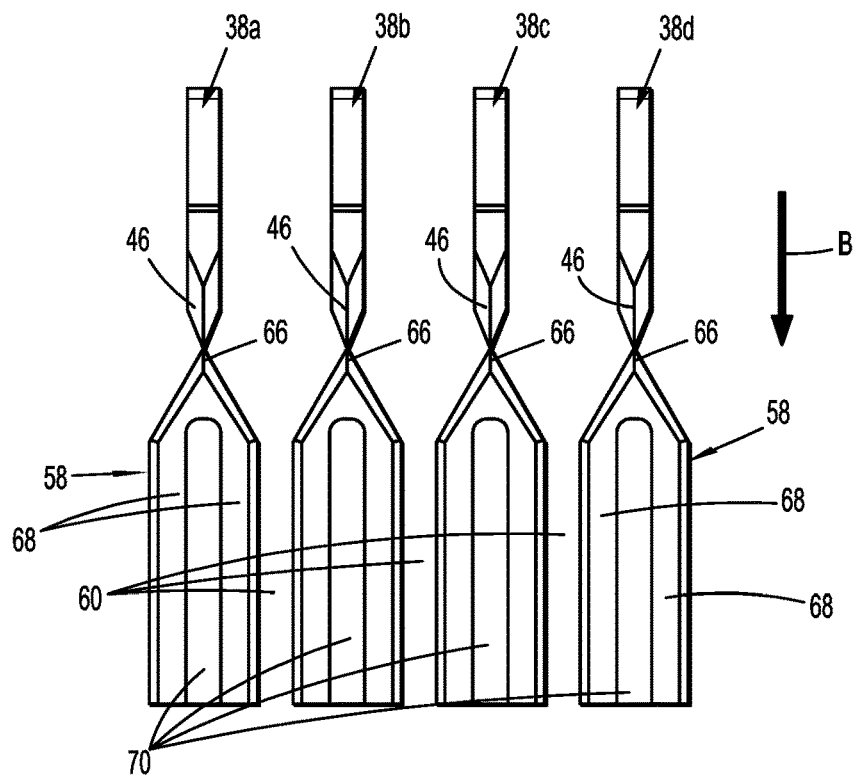
FIG. 16 is a schematic view of splines of the anvil assembly and the splines of the shell assembly of the surgical stapling device shown in FIG. 1 as the splines crash.
Figure 17:
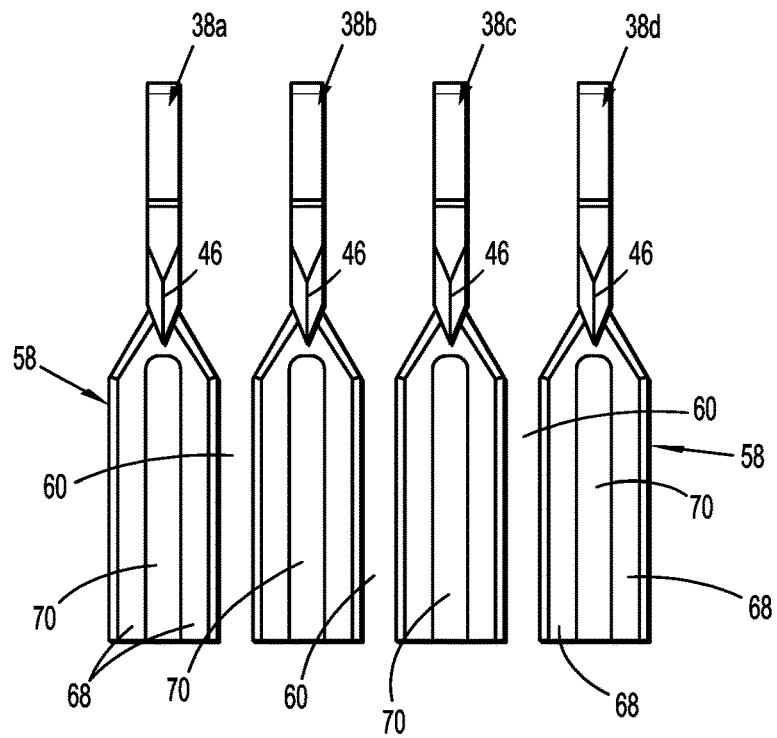
FIG. 17 is a schematic view of splines of the anvil assembly and the splines of the shell assembly of the surgical stapling device shown in FIG. 1 as the splines of the anvil assembly penetrate into the splines of the shell assembly.
Figure 18:
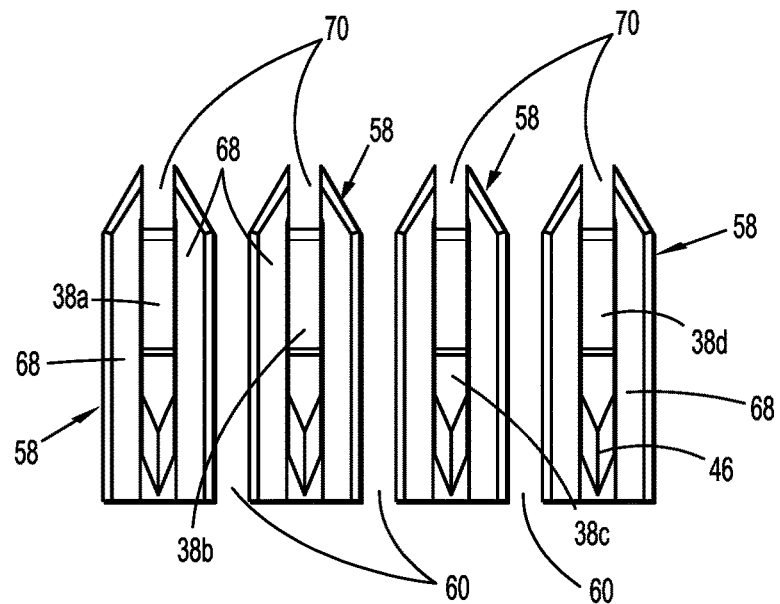
FIG. 18 is a schematic view of the splines of the anvil assembly of the surgical stapling device shown in FIG. 1 and the splines of the shell assembly of the surgical stapling device shown in FIG. 1 after the splines of the anvil assembly have penetrated the splines of the shell assembly and moved into secondary channels defined by the splines of the shell assembly.
Figure 19:
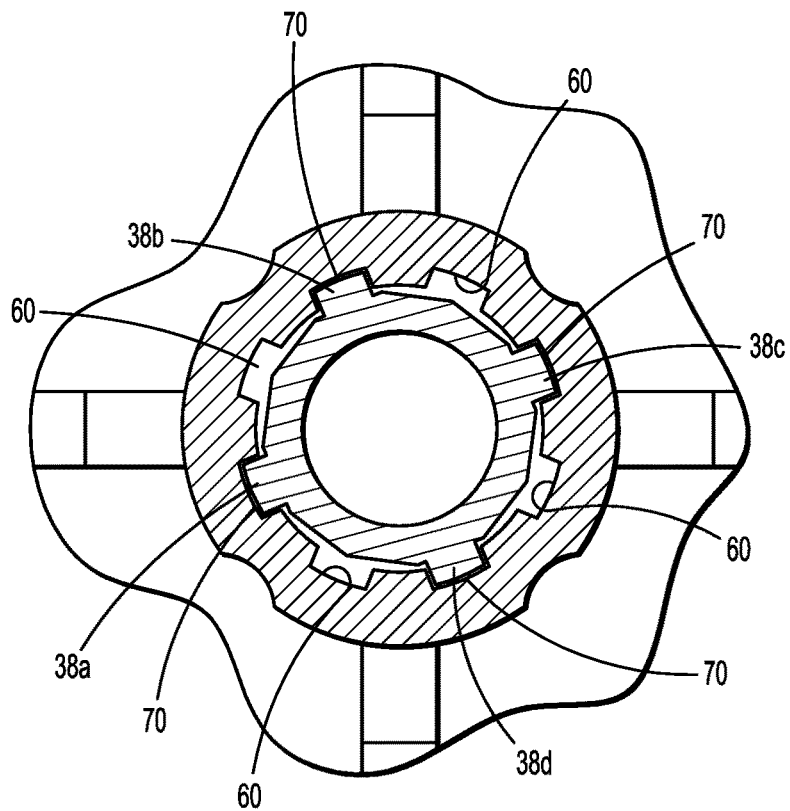
FIG. 19 is cross-sectional view taken through the splines of the anvil and shell assemblies as the splines of the anvil assembly move into the secondary channels of the shell assembly.

Referring to FIGS. 16-19, as the anvil shaft 36 is drawn into the inner bore 56 of the shell housing 50 in the direction indicated by arrow "C" in FIG. 16, if the apex 46 of the splines 38a-d are positioned to engage head on or "crash" with the apex 66 of the A-frame splines 58 (FIG. 16), the apex 46 of the splines 38a-d will penetrate the A-frame splines 58 (FIG. 17) such that the splines 38a-d will be directed into the secondary channels 70 defined between the side walls 68 of the A-frame splines 58 (FIG.). In this position, the staple receiving slots 28 (FIG. 1) of the staple cartridge 18a are aligned with the staple deforming recesses formed on the anvil surface 34a such that staples ejected from the staple receiving slots 28 will be properly deformed within the staple deforming recesses formed on the anvil surface 34a when the stapling device 10 is fired.

By providing A-frame splines 58 on the shell housing 50 that define secondary channels 70 that are positioned beneath the apex 66 of the A-frame splines 58, the combination of the splines 38a-d on the anvil shaft 36 of the anvil assembly 20 and the A-frame splines 58 on the shell housing 50 of the shell assembly 18 can properly align the anvil assembly 20 and the shell assembly 18 even when the splines crash.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
an approximation assembly including an anvil retainer;
an anvil assembly including an anvil shaft having at least one anvil spline and an anvil head having an anvil surface defining a plurality of staple deforming recesses, the anvil head being supported on a distal portion of the anvil shaft; and
a shell assembly including a shell housing having an inner housing portion defining a bore, a plurality of shell splines supported on the inner housing portion within the bore, each of the plurality of shell splines having spaced side walls and a pair of tapered surfaces that intersect at an apex extending distally from the spaced side walls and, each of the spaced side walls of adjacent shell splines of the plurality of shell splines defining a primary channel and the spaced side walls of each of the plurality of shell splines defining a secondary channel, the secondary channel of each of the shell splines defining a longitudinal axis that is positioned in axial alignment with the apex of the shell spline, wherein the primary and secondary channels are dimensioned to receive one of the at least one anvil splines.

2. The surgical stapling device of claim 1, wherein the tapered surfaces of each of the shell splines are positioned on a distal portion of the shell spline.

3. The surgical stapling device of claim 1, wherein the at least one anvil spline includes a pair of tapered surfaces that intersect at an apex.

4. The surgical stapling device of claim 1, wherein the primary and secondary channels are positioned to receive the at least one anvil spline to properly align the anvil assembly with the shell assembly.

5. The surgical stapling device of claim 1, wherein the apex of each of the shell splines is constructed to fracture upon engagement with the apex of the at least one anvil spline to allow passage of the at least one anvil spline into a respective one of the secondary channels.

6. The surgical stapling device of claim 1, wherein the at least one anvil spline includes a plurality of anvil splines.

7. The surgical stapling device of claim 1, wherein the tapered surfaces of each of the plurality of shell splines is configured to cam the at least one anvil spline into a respective primary channel when the apex of the at least one anvil spline engages one of the tapered surfaces.

8. The surgical stapling device of claim 1, wherein the shell assembly includes a staple cartridge supported within the shell housing.

9. A shell assembly for a circular stapling device comprising:
   a shell housing having an inner housing portion defining a bore, a plurality of shell splines supported on the inner housing portion within the bore, each of the plurality of shell splines having a pair of tapered surfaces that intersect at an apex and spaced side walls, each of the spaced side walls of adjacent shell splines of the plurality of shell splines defining a primary channel and the spaced side walls of each of the plurality of shell splines defining a secondary channel defining a longitudinal axis that is positioned in axial alignment with the apex of the respective shell spline, wherein the primary and secondary channels are dimensioned to receive an anvil spline of a surgical stapling device.

10. The shell assembly of claim 9, wherein the tapered surfaces of each of the shell splines is positioned on a distal portion of the shell spline.

11. The shell assembly of claim 9, wherein the primary and secondary channels are positioned to receive the anvil spline to properly align an anvil assembly of a surgical stapling device with the shell assembly.

12. The shell assembly of claim 9, wherein the apex of each of the shell splines is constructed to fracture upon engagement with an apex of the anvil spline to allow passage of the anvil spline into one of the secondary channels.

13. The shell assembly of claim 9, wherein the tapered surfaces of each of the plurality of shell splines is configured to cam the anvil spline into one of the primary channels when an apex of the anvil spline engages one of the tapered surfaces.

14. The shell assembly of claim 9, further including a staple cartridge supported within the shell housing.

15. A tool assembly for a surgical stapling device comprising:
   an anvil assembly including an anvil shaft having at least one anvil spline and an anvil head having an anvil surface defining a plurality of staple deforming recesses, the anvil head being supported on a distal portion of the anvil shaft; and
   a shell assembly including a shell housing having an inner housing portion defining a bore, a plurality of shell splines supported on the inner housing portion within the bore, each of the plurality of shell splines having a pair of tapered surfaces that intersect at an apex and spaced side walls, each of the spaced side walls of adjacent shell splines of the plurality of shell splines defining a primary channel and the spaced side walls of each of the plurality of shell splines defining a secondary channel defining a longitudinal axis that is positioned in axial alignment with the apex of the respective shell spline, wherein the primary and secondary channels are dimensioned to receive one of the at least one anvil splines.

16. The tool assembly of claim 15, wherein the tapered surfaces of each of the shell splines is positioned on a distal portion of the shell spline.

17. The tool assembly of claim 15, wherein the at least one anvil spline includes a pair of tapered surfaces that intersect at an apex.

18. The tool assembly of claim 15, wherein the primary and secondary channels are positioned to receive the at least one anvil spline to properly align the anvil assembly with the shell assembly.

19. The tool assembly of claim 15, wherein the apex of each of the shell splines is constructed to fracture upon engagement with the apex of the at least one anvil spline to allow passage of the at least one anvil spline into a respective one of the secondary channels.

20. The tool assembly of claim 15, wherein the tapered surfaces of each of the plurality of shell splines is configured to cam the at least one anvil spline into a respective primary channel when the apex of the at least one anvil spline engages one of the tapered surfaces.

\* \* \* \* \*